(12) United States Patent
Alhallami

(10) Patent No.: US 9,839,606 B2
(45) Date of Patent: Dec. 12, 2017

(54) FORMULATION FOR TREATMENT OF HAIRS

(71) Applicant: OSMA Cosmetics & Laboratories AG, Weggis (CH)

(72) Inventor: Omran Alhallami, Weggis (CH)

(73) Assignee: OSMA COSMETICS & LABORATORIES AG, Weggis (CH)

( * ) Notice: Subject to any disclaimer, the term of this patent is extended or adjusted under 35 U.S.C. 154(b) by 0 days.

(21) Appl. No.: 15/186,042

(22) Filed: Jun. 17, 2016

(65) Prior Publication Data

US 2016/0287511 A1    Oct. 6, 2016

Related U.S. Application Data

(63) Continuation of application No. PCT/EP2014/077212, filed on Dec. 10, 2014.

(30) Foreign Application Priority Data

Dec. 19, 2013  (CH) ...................... 2103/13

(51) Int. Cl.
| | | |
|---|---|---|
| *A61K 36/00* | (2006.01) | |
| *A61K 8/97* | (2017.01) | |
| *A61K 36/82* | (2006.01) | |
| *A61K 36/889* | (2006.01) | |
| *A61K 35/644* | (2015.01) | |
| *A61K 36/63* | (2006.01) | |
| *A61K 8/98* | (2006.01) | |
| *A61Q 5/00* | (2006.01) | |
| *A61Q 7/00* | (2006.01) | |

(52) U.S. Cl.
CPC ............. *A61K 8/97* (2013.01); *A61K 8/988* (2013.01); *A61K 35/644* (2013.01); *A61K 36/63* (2013.01); *A61K 36/82* (2013.01); *A61K 36/889* (2013.01); *A61Q 5/006* (2013.01); *A61Q 7/00* (2013.01)

(58) Field of Classification Search
None
See application file for complete search history.

(56) References Cited

U.S. PATENT DOCUMENTS

2009/0264291 A1  10/2009 Soudant et al.
2010/0178409 A1* 7/2010 Kashima ............... C12G 3/04
                                                          426/538

FOREIGN PATENT DOCUMENTS

| CN | 102225043 A | | 10/2011 |
|----|-------------|---|---------|
| CN | 102948839 A | * | 3/2013 |
| CN | 103289860 A | * | 9/2013 |
| DE | 3442961 C1 | | 8/1985 |
| DE | 19948652 A1 | | 4/2001 |
| EP | 2095811 A1 | | 9/2009 |
| GB | 2478967 A | | 9/2011 |
| KR | 2008094305 A | * | 10/2008 |
| KR | 101319097 B1 | * | 10/2013 |
| WO | 9955349 A1 | | 11/1999 |
| WO | 2004056328 A1 | | 7/2004 |

OTHER PUBLICATIONS

Al-Shahib et al, Fatty acid content of the seeds from 14 varieties of date palm Phoenix dactylifera L. International Journal of Food Science & Technology (2003), vol. 38, No. 6, pp. 709-712.*
"Dates", Aug. 19, 2013, pp. 1-2, http://web.archive.org/web/20130819183938/http://www.healthaliciousness.com/fruits/date.php, retrieved on Feb. 27, 2014.
Al-Waili, "Therapeutic and Prophylactic Effects of Crude Honey on Chronic Seborrheic Dermatitis and Dandruff", European Journal of Medical Research, 2001, pp. 306-308, vol. 6.
Bauza et al., "Date Palm Kernel Extract Exhibits Antiaging Properties and Significantly Reduces Skin Wrinkles", International Journal of Tissue Reactions, 2002, pp. 131-136, vol. 24, No. 4.
English Abstract of CN 102885741A.
Esfandiari et al., "The Effects of Tea Polyphenolic Compounds on Hair Loss Among Rodents", Journal of the National Medical Association, Jun. 2005, pp. 816-818, vol. 97, No. 6.
Iftikhar et al., "Effect of Date Palm Pollen (DPP) on Serum Testosterone Levels in Prepubertal Albino Rats", Pakistan Journal of Medical and Health Sciences, Oct. 2011, pp. 639-644, vol. 5, No. 4.
International Preliminary Report on Patentability (Chapter I) for PCT/EP2014/077212 dated Jun. 21, 2016.
International Search Report and Written Opinion for PCT/EP2014/077212 dated Jun. 25, 2015.
Kwon et al., "Human Hair Growth Enhancement in Vitro by Green Tea Epigallocatechin-3-Gallate (EGCG)", Phytomedicine, 2007, pp. 551-555, vol. 14.
Lachenmeier, "Safety Evaluation of Topical Applications of Ethanol on the Skin and Inside the Oral Cavity", Journal of Occupational Medicine and Toxicology, Nov. 13, 2008, 16 pages, vol. 3, No. 26.
Sanderson, "Natural History of the Date Palm Phoenix Dactylifera", Aug. 2001, pp. 1-7, http://web.archive.org/web/20121219074846/http://enhg.4t.com/articles/date.htm, retrieved Feb. 2, 2014.

* cited by examiner

*Primary Examiner* — Qiuwen Mi
(74) *Attorney, Agent, or Firm* — Thompson Coburn LLP

(57) ABSTRACT

A formulation for the treatment of hair, in particular for treatment of hair loss and dandruff, useful as a lotion and/or a spray. The formulation comprises at least dates, date seeds, and ethanol from fermented dates and date seeds.

6 Claims, 2 Drawing Sheets

FORMULATION FOR TREATMENT OF HAIRS

CROSS-REFERENCE TO RELATED APPLICATIONS

The present application is a continuation application claiming the benefit of PCT/EP2014/077212, filed Dec. 10, 2014, which claims the benefit of Swiss Patent Application 02103/13, filed Dec. 19, 2013, each of which is incorporated herein by reference in its entirety.

FIELD OF THE INVENTION

The invention concerns a formulation for treatment of hairs, in particular for treatment of hair loss and dandruff, useful as a lotion and/or spray.

BACKGROUND OF INVENTION

Hair loss or Alopecia in its various forms is a global widespread problem for both men and women. Androgenetic alopecia (AGA) may affect up to 70% of men and 40% of women at some point in their lifetime. While men typically present with a distinctive alopecia pattern involving hairline recession and vertex balding, women normally exhibit a diffuse hair thinning over the top of their scalps. The treatment standard in dermatology clinics continues to be minoxidil and finasteride with hair transplantation as a surgical option.

Alopecia areata (AA) is the patchy loss of hair on the scalp or body. It can occur at any age and affects 1% of the population, most commonly children. The reasons for its development are not fully understood. Although not life threatening, the hair loss can be psychologically traumatic. Scientists think AA is an autoimmune disease where white blood cells from the immune system attack hair follicles and keep them from producing hairs. Autoimmune diseases occur when a human's immune system mistakenly thinks that part of his or her own tissue is diseased. The tissue is then attacked. The end result depends on how effectively the tissue defends itself as it tries to grow back normally. Treatment depends on the extent of the disease, and the age of the patient. For small disease patches, intralesional steroid injections (Kenalog®) are the best approach. This is injected with a tiny needle directly into the patches on the scalp with injections spread over affected areas. Injections are repeated every 4 to 6 weeks. The amount of steroid used is safe as long as reasonable limits are not exceeded. Other options include topical minoxidil (Rogaine) and prescription steroid lotions. These are better for moderately extensive cases.

For more severe widespread disease, options include short contact anthralin treatment (Micanol) and contact hypersensitization. The most effective treatment currently available is contact hypersensitization with some studies showing a 40% success rate. It causes local dermatitis (rash) with swollen lymph nodes. Treatment needs to be continued from months to a year or so to get a good result.

Each hair sits in a cavity in the skin called a follicle. The average human head has about 100,000 hair follicles. Each follicle can grow about 20 individual hairs in a person's lifetime. Hair grows about an inch (2.54 cm) every couple of months. Each hair grows for 2 to 6 years, remains at that length for a short period, then falls out. Most people shed 50 to 150 hairs a day. A new hair soon begins growing in its place.

The hair follicle cycle consists of stages of rest (telogen), hair growth (anagen), follicle regression (catagen), and hair shedding (exogen). The entire lower epithelial structure is formed during anagen, and regresses during catagen. The transient portion of the follicle consists of matrix cells in the bulb that generate seven different cell lineages, three in the hair shaft, and four in the inner root sheath (IRS), see FIG. 1.

The typical pattern of male baldness begins at the hairline. The hairline gradually moves backward (recedes) and forms an "M" shape. Eventually, the hair becomes finer, shorter, and thinner, and creates a U-shaped (or horseshoe) pattern of hair around the sides of the head.

Medications that treat male pattern baldness include:
Minoxidil (ROGAINE), a solution that is applied directly to the scalp to stimulate the hair follicles. It slows hair loss for many men, and some men grow new hair. Hair loss returns when you stop using this medicine.
Finasteride (PROPECIA, PROSCAR), a pill that interferes with the production of a highly active form of testosterone that is linked to baldness. It slows hair loss. It works slightly better than minoxidil. Hair loss returns when you stop using this medicine.

Hair transplants consist of removing tiny plugs of hair from areas where the hair is continuing to grow and placing them in areas that are balding. This can cause minor scarring and possibly, infection. The procedure usually requires multiple sessions and may be expensive.

Suturing hair pieces to the scalp is not recommended. It can result in scars, infections, and an abscess of the scalp. The use of hair implants made of artificial fibers was banned by the FDA because of the high rate of infection.

Although the mechanism is not clearly understood, genetics and hormones are thought to be involved in pattern baldness. In pattern baldness, heredity appears to play a significant role as pattern baldness on either side of the family increases the risk of balding. Excessive amounts of a hormone known as dihydrotestosterone ("DHT") is also thought to adversely affect hair follicles. DHT binds to androgen receptors in the hair follicles to regulate normal hair growth. Testosterone, a hormone that is present in high levels in males after puberty, is converted to DHT by an enzyme called 5-alpha reductase. As men mature, their bodies produce more testosterone resulting in increased amounts of DHT. Androgen receptor activity increases, slowing down hair production and producing weaker, shorter hair each time the hair regrows.

Other causes of temporary hair loss include disease, diabetes, lupus and thyroid disorder, poor nutrition, medications, certain drugs, medical treatments, childbirth, hair treatments and scalp infections.

Baldness, whether permanent or temporary, cannot be cured, but treatments are available to help promote hair growth or hide hair loss. However, results vary and side effects can be disconcerting.

Minoxidil (ROGAINE), available over-the-counter, is a liquid that is dispensed onto the scalp twice daily to regrow hair and to prevent further loss. Some people experience some hair regrowth, a slower rate of hair loss, or both. However, new hair resulting from minoxidil use may be thinner and shorter than previous hair. In addition, side effects can include irritation of the scalp.

Finasteride (PROPECIA) is a prescription medication used to treat male-pattern baldness taken daily in pill form. Finasteride inhibits the production of the male hormone dihydrotestosterone. Many people taking finasteride experience a slowing of hair loss, and some may show some new hair growth. Results may take up to several months to manifest. Side effects may include diminished sex drive and sexual function. In addition, Finasteride is not approved for use by women. In fact, it poses significant danger to women of childbearing age and should not be handled by pregnant women.

Surgical procedures, such as hair transplants and scalp reduction surgery, have also been used to treat hair loss. Hair transplants involve taking tiny plugs of skin, each containing one to several hairs, and implanting them into the balding areas. However, effective treatment may require several sessions. Scalp reduction involves decreasing the area of bald skin by surgically removing a balding area and closing the gap with hair-covered scalp. However, these surgical procedures are expensive, can be painful, and may require several procedures. In addition, risks include infection and scarring.

Thus, a safe, effective, cost-effective, easy treatment for preventing hair loss or promoting hair growth is still needed.

SUMMARY OF INVENTION

The object of the present invention is directed toward solution formulations for treatment of hairs, preventing hair loss, countering dandruff, and stimulating hair growth, namely for humans and non-medical (cosmetic) use.

An embodiment of the invention is directed to a method for producing a formulation for the treatment of hair, the method comprising: mixing a date-based ethanol-containing distillate, a date seed infusion, a green tea infusion, honey, and water to form an encompassing mixture; filtering the encompassing mixture to remove solids that may be present in the encompassing mixture; and mixing the filtered encompassing mixture with olive oil to form the formulation for the treatment of hair.

An embodiment of the invention is directed to a formulation for the treatment of hair, wherein the formulation is made by the method of the immediately preceding paragraph.

An embodiment of the invention is directed to a formulation for the treatment of hair, the formulation comprising a date-based ethanol-containing distillate and a date seed infusion.

An embodiment of the invention is directed to a method of treating scalp and hair to reduce or prevent dandruff and hair loss as needed, the method comprising contacting the scalp and hair with an effective amount of the formulation of the immediately preceding paragraph for an effective duration.

An embodiment of the invention is directed to a method of treating scalp and hair to reduce or prevent dandruff and hair loss as needed, the method comprising:

contacting the scalp and hair with a first effective amount of a first formulation for a first effective duration, wherein the first formulation is a lotion that consists of an encompassing mixture and olive oil at a volume ratio of about 9:1, wherein the encompassing mixture consists of a date-based ethanol-containing distillate, a date seed infusion, a green tea infusion, honey, and water at a volume ratio of about 1:0.07:0.07:0.05-0.1:0.1-0.05, wherein the date-based ethanol-containing distillate comprises at least 82% by volume ethanol, and wherein the date-based ethanol-containing distillate is no more than 60% by volume of the first formulation;

removing the first formulation from the scalp and hair; and after said removal of the first formulation, contacting the scalp and hair with a second effective amount of a second formulation for a second effective duration, wherein the second formulation is a spray that consists of 2 to 5 percent by volume of the date-based ethanol-containing distillate, and the date seed infusion.

DETAILED DESCRIPTION OF INVENTION

Figure 1:
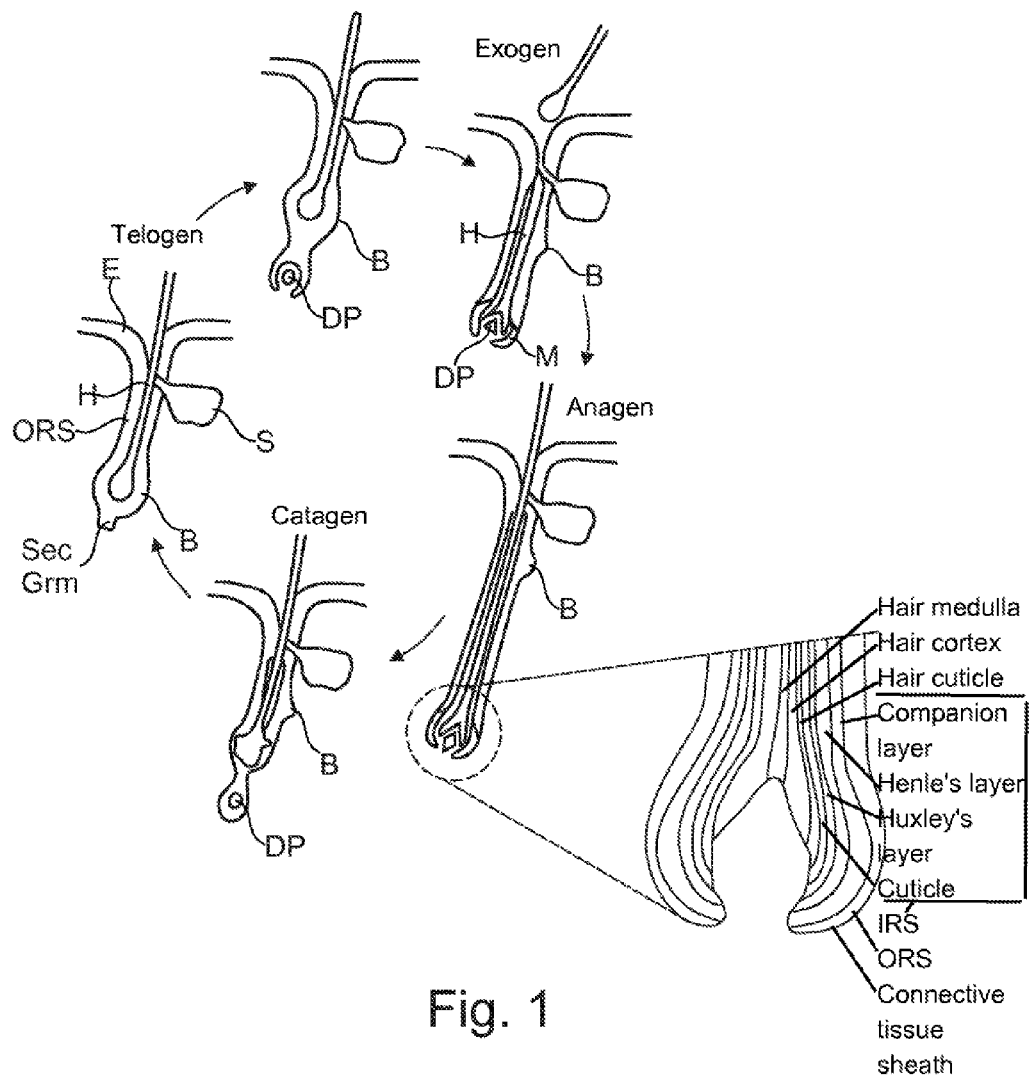
FIG. 1 shows the epithelial structure of hair, wherein B identifies the bulge, DP identifies the dermal papilla, H identifies the hair, IR identifies the inner root sheath, M identifies the matrix, ORS identifies the outer root sheath, S identifies the sebaceous gland, and Sec Grm identifies the secondary germ.

The formulation is a mixture of completely organic materials with its phytochemicals, dates, date seeds, and date molasses. Preferentially also including olive oil and/or honey and/or green tea leaves, in addition to several components of the date palm tree, using ethanol extracted from dates, date molasses and date seeds as a solvent and a carrier with its rich ingredients.

Date Palm Tree/Genus: *Phoenix*.

*Phoenix Dactylifera* L.

Dates are considered the oldest cultivated fruit in the world. Fossils show date palm trees thrived 50 million years ago.

Date fruits have been ascribed to have many favorable properties when consumed either alone or in combination with other herbs. Although fruit of the date palm served as the staple food for millions of people around the world for several centuries, studies on the health benefits are inadequate and hardly recognized as a healthy food by the health professionals and the public. In recent years, an explosion of interest in the numerous health benefits of dates has led to many in vitro and animal studies as well as the identification and quantification of various classes of phytochemicals. On the basis of available documentation in the literature on the nutritional and phytochemical composition, it is apparent that the date fruits are highly nutritious and may have several potential health benefits.

Lineage

The evolution of land plants is characterized by whole genome duplications (WGD), which drove species diversification and evolutionary novelties. Detecting these events is especially difficult if they date back to the origin of the plant kingdom. Established methods for reconstructing WGDs include intra- and inter-genome comparisons, KS age distribution analyses, and phylogenetic tree constructions. The present invention predicts WGD *Phoenix dactylifera*, and a triplication or two WGDs for *Gossypium raimondii*. The data shows another myosin duplication in the ancestor of the angiosperms that could be either the result of a single gene duplication or a remnant of a WGD.

Genetics

"Repetitive Sequences": *P. dactylifera* mt genome has much less repetitive sequences as compared to those of other known angiosperms. Only one long palindromic sequence with a repeat unit longer than 1000 bp was identified and no inverted repeats were found. Overall, long repeats (>50 bp) only account for 2.3% of the genome, even lower than that of *Vitis* (2.9%) and *Vigna radiata* (2.7%), which contain the lowest repeat contents among sequenced angiosperm mt genomes, whereas *Tripsacum* and *Oryza* contain 36.4% and 30.4% long repetitive sequences, respectively.

Relevance of Genetics in the Invention

Given the information specified about *P. dactylifera*, genetic background, and ancient human record, one can only assume whether from an evolutionary standpoint or from a genetic one, that humans have been exposed to dates and date palms from the dawn of time, and share a lot of similar ancestry genetically.

One of the main reasons for pattern baldness in males is testosterone imbalance. Date Palm Pollen extract (DPP) restored spermatogenesis and attenuated the toxic effects of Cd on the reproductive system to the levels observed in the control animals. These findings support the hypothesis that the testis is particularly sensitive to Cd, which can cause testicular damage and infertility. Treatment with DPP can ameliorate the deleterious effects of Cd, probably by activating testicular endocrine and antioxidant systems. In addition, four cultivars (Gondi, Gasbi, Khalt Dhahbi, and Rtob Ahmar) of Tunisian date palm (*Phoenix dactylifera* L.) fruits at three maturation stages, besser, rutab and tamr, were analyzed for their antioxidant activities (AA) using 2,2'-azino-bis (3-ethylbenzothiazoline-6-sulfonic acid) and 2,2-diphenyl-1-picrylhydrazyl radicals cation, and reducing power (RP) methods. The total phenolic (TPC), total flavonoid (TFC), and condensed tannins (CTC) contents were measured. Results showed that all samples have the highest TPC, TFC, CTC, and AA at besser stage. A significant correlation ($p<0.05$) was found between TPC, TFC, CTC and AA during ripening. Sixteen phenolic compounds were identified and quantified by HPLC. The major ones were caffeic, ferulic, protocatechuic, and catechin for the majority of cultivars.

The data as found indicates that common date fruits are rich in natural antioxidants that might be more widely used by both the general population and the food industry as a source of bioactive human health promoter phytochemicals.

Dates and Date Seeds and Date-Based Ethanol

Given the significance of all the above, the main claim of the invention is the introduction of dates, date seeds and using ethanol fermented and extracted from dates and seeds and several components of the date palm tree (*P. dactylifera* L.) or other palms in the *Phoenix* genus to combat hair loss and promote hair growth. Genetically, palm tree extracts (i.e., through the dates, seeds or ethanol fermented thereof) have the best chance and are the most effective in treating alopecia conditions.

Such extracts have shown excellent anti-allergic properties, some polyphenols in the date may reduce mite-induced allergic symptoms in mice via a decrease in the number of IgE-producing plasma cells and high-affinity IgE receptor-expressing mast cells.

Date (*Phoenix dactylifera* L.) fruit soluble phenolics composition and anti-atherogenic properties were examined in nine diverse Israeli grown varieties. Ethanol and acetone extracts of "Amari", "Barhi", "Deglet Noor", "Deri", "Hadrawi", "Hallawi", "Hayani", "Medjool", and "Zahidi" fruit were analyzed for phenolics composition by RP-HPLC and tested for anti-atherogenicity by measuring their effects on LDL susceptibility to copper ion-, and free radical-, induced oxidation, and on serum-mediated cholesterol efflux from macrophages.

The most frequently detected phenolics were hydroxybenzoates, hydroxycinnamates, and flavonols. Significant differences in phenolics composition were established between varieties as well as extraction solvents. All extracts inhibited LDL oxidation, and most extracts also stimulated cholesterol removal from macrophages.

Considerable varietal differences were measured in the levels of the bioactivities. Also, acetone extracts exhibited a significantly higher anti-atherogenic potency for most varieties. The presence of soluble ingredients with antiatherogenic capacities in dates and the possible involvement of phenolics are discussed, which can explain the vascular effects observed on the scalp and follicles after the product is applied.

As for the anti-inflammatory properties, percentages of seed, moisture, fructose, glucose, soluble protein, and fiber in Ajwa dates were 13.24, 6.21, 39.06, 26.35, 1.33, and 11.01, respectively. The ethyl acetate, methanoic, and water extracts of Ajwa dates, active at 250 µg/mL in the MTT assay, inhibited lipid peroxidation (LPO) by 88, 70, and 91% at 250 µg/mL and cyclooxygenase enzymes COX-1 by 30, 31, and 32% and COX-2 by 59, 48, and 45% at 100 µg/mL, respectively. Bioactivity-guided purifications afforded compounds 1-7, in addition to phthalates and fatty acids. Compounds 1-3 showed activity at 100 µg/mL in the MTT assay; inhibited COX-1 enzyme by 59, 48, and 50% and COX-2 enzyme by 60, 40, and 39% at 50 µg/mL; and inhibited LPO by 95, 58, and 66% at 100 µg/mL, respectively. The soluble protein fraction was also very active in both antioxidant and anti-inflammatory assays, thus acting as an anti-inflammatory agent combating the autoimmune attack of the follicles, the main culprit behind alopecia areata.

Dates, Date Seeds, Mineral Composition

Dates contain per 100 g (64 mg Calcium, 0.9 Iron, 54 mg Magnesium, 62 mg Phosphorus, 696 mg Potassium, 1 mg Sodium, 0.44 mg Zinc). These products from their natural origin have a great effect on the human body.

Calcium and phosphorus are critical for communicating essential information among cells, which is a component of the scope of the invention.

Sodium is responsible for generation of nervous impulses and finer regulation of fluid balance.

The role of magnesium is contraction and relaxation of muscles, function of certain enzymes in the body, production and transport of energy, and production of proteins.

Zinc is important for healthy hair. Insufficient zinc levels may result in loss of hair, hair that looks thin and dull and that goes grey early.

Several studies have shown that high potassium concentrations protect inner and outer hair cells from ischemia-induced damage in newborn rat culture.

Date seed oil inhibits hydrogen peroxide-induced oxidative stress in human epidermal keratinocytes.

Oxidative stress has been implicated in various skin diseases through the generation of reactive oxygen species and the depletion of endogenous antioxidant systems. The administration of antioxidants is reportedly helpful, notably to enhance the healing process. To protect the skin against oxidative damages, the inventor has studied the effect of new "date seed oil" (DSO). This oil may serve as a potential source of natural antioxidants such as phenols and tocopherols.

Findings demonstrate that DSO is an efficient extract that is able to prevent keratinocytes oxidative damage induced by $H_2O_2$ exposure and may thus be a potential promising candidate, as a chemopreventive agent, in the development of keratinocytes-related pathologies.

Date seed oil has high concentration of oleic acid that acts as an emollient to the solution in addition to making the external skin epidermis softer and more pliable, which helps with the penetration of the solution.

Olive Oil

Olive oil has a concentration of 14.35 mg of vitamin E per 100 g. With age, the production of free radicals increases, while the endogenous defense mechanisms decrease. This imbalance leads to the progressive damage of cellular structures, presumably resulting in the ageing phenotype. The ageing phenotype of hair manifests as a decrease of melanocyte function or graying, and a decrease in hair production or alopecia, non-enzymatic antioxidative molecules, like vitamin E, vitamin C, glutathione, ubiquinone, protect it from free radicals by reducing and neutralizing them.

In addition, scientists tested olive oil, avocado oil, meadow foam seed oil, sunflower oil, and jojoba oil. Their results showed that straight chain glycerides like olive oil easily penetrate into the hair. Polyunsaturated oils, like jojoba oil, are more open in their structure so they don't pass through the layers of cuticles very well.

Honey

In addition to having a high concentration of potassium of 52 mg per 100 g, honey has antibacterial, antifungal and antioxidant activities and has high nutrient value. In a study that investigated the potential use of topical application of crude honey in the management of seborrheic dermatitis and dandruff, thirty people with chronic seborrheic dermatitis of the scalp, face and front of the chest were entered into the study. Twenty people were males and 10 were females; their ages ranged between 15 and 60 years. The people had scaling, itching and hair loss. The lesions were scaling macules, papules and dry white plaques with crust and fissures. The people were asked to apply diluted crude honey (90% honey diluted in warm water) every other day on the lesions with gentle rubbing for 2-3 minutes. Honey was left on for 3 hours before gentle rinsing with warm water. The people were followed daily for itching, scaling, hair loss and the lesions were examined. Treatment was continued for 4 weeks. The improved people were included in a prophylactic phase, lasting six months. Half of the people were treated with the topical honey once weekly and the other half served as a control group. All the people responded markedly with the application of honey. Itching was relieved and scaling had disappeared within one week. Skin lesions were healed and disappeared completely within 2 weeks. In addition, people showed subjective improvement in hair loss. None of the 15 people treated with the honey application once weekly for six months showed a relapse while the 12/15 patients who had no prophylactic treatment with honey experienced a relapse of the lesions 2-4 months after stopping treatment. It might be concluded that crude honey could markedly improve seborrheic dermatitis and associated hair loss and prevent relapse when applied weekly.

Green Tea Leaves

Fresh tea leaves are unusually rich in the flavonol group of polyphenols known as catechins which may constitute up to 30% of the dry leaf weight. Other polyphenols include flavonols and their glycosides, and depsides such as chlorogenic acid, coumarylquinic acid, and one unique to tea, theogallin (3-galloylquinic acid). Caffeine is present at an average level of 3% along with very small amounts of the other common methylxanthines, theobromine, and theophylline. The amino acid theanine (5-N-ethylglutamine) is also unique to tea. Tea accumulates aluminum and manganese. In addition to the normal complement of plant cell enzymes, tea leaves contains an active polyphenol oxidase which catalyzes the aerobic oxidation of the catechins.

Its potential beneficial effects such as anti-cancer and anti-oxidant properties are believed to be mediated by epigallocatechin-3-gallate (EGCG), a major constituent of polyphenols. It was reported that EGCG might be useful in the prevention or treatment of androgenetic alopecia by selectively inhibiting 5 alpha-reductase activity. A study was undertaken to measure the effect of EGCG on hair growth in vitro and to investigate its effect on human dermal papilla cells (DPCs) in vivo and in vitro. EGCG promoted hair growth in hair follicles ex vivo culture and the proliferation of cultured DPCs. The growth stimulation of DPCs by EGCG in vitro may be mediated through the upregulations of phosphorylated Erk and Akt and by an increase in the ratio of Bcl-2/Bax ratio. Similar results were also obtained in vivo dermal papillae of human scalps. Thus, the inventor suggests that EGCG stimulates human hair growth through these dual proliferative and anti-apoptotic effects on DPCs.

In an experimental study, 60 female Balb/black mice, which had developed spontaneous hair loss on the head, neck and dorsal areas, were randomly assigned into two equal groups; A (experimental) and B (control). Group A received 50% fraction of polyphenol extract from dehydrated green tea in their drinking water for six months. Group B received regular drinking water. Both groups were fed regular rodent diets (Purina Rodent Chow 5001) and housed individually in polycarbonate cages.

The results showed that 33% of the mice in experimental Group A, who received polyphenol extract in their drinking water, had significant hair regrowth during six months of treatment (p=0.014). No hair growth was observed among mice in the control group, which received regular water.

Ethanol

All of the above mentioned components need a penetration enhancer to accelerate and fortify their effects. Urea, sodium dodecyl sulfate, dimethylsulfoxide (DMSO), ethanol (75 and 96%), NaCl, and peppermint and orange oils were used as penetration enhancers. Results showed that ethanol (75%), DMSO, and peppermint oil (ethanolic solution) were able to significantly reduce TRT up to two times from about 6 to 3.5 minutes.

Ethanol used in the invention is extracted from dates, date seeds and other *P. dactylefira* L. parts, given the importance of their composition, to be further distilled into the product.

Ethanol concentrations never exceeded 60% to avoid hair damage, while benefiting from ethanol as the best penetration enhancer agent available.

As far as the previously mentioned ingredients are concerned, the cultivated items used in the solution formulation should be the best of their respective species. They are completely organic, and all of them are even safely edible.

The highest quality ingredients of the formulation solution include: Khalas dates, Alsidr or Alsamer honey, Napulsi olive oil, and Ceylon dried green tea leaves.

It is to be understood, however, that the same of equivalent results could be accomplished by different types of species or lower quality ones, or different mixing ratios or preparation techniques. This is also intended to be encompassed within the scope of the invention.

EXAMPLE

Mixing and Preparation of the Hair Formulation Solution

For the creation of 7.142 Liter of the final lotion/solution:
A) 10 kg of dates with their seeds are put into a mixing container.

B) 1 kg of date molasses, in addition to 40 liters tap water and 14-18 grams of the yeast "*Saccharomyces cerevisiae*" is added to the mix.

C) The mixture is left for one week or more, depending on temperature and surrounding environment, for fermentation.

D) The fermented result, which is rich in the active ingredients found in dates and seeds, will be distilled efficiently similar to spirit distillation to get rid of any trace of methanol, in preferably a copper boiler that would combat the smells and be the least susceptible for germs to thrive, and reduce unwanted acid content as well as cyanide and ethyl carbamate levels.

E) The resulting mixture will be distilled again to reduce the water content and to generate more ethanol and distilled to a 5:1 ethanol-distilled water solution, of at least 82 vol.-%, referred to as SI.

F) Simultaneously, 30-40 grams of date seeds, depending on variety and size, are crushed in another container and dried via exposure to the sun or via heating.

G) The dried seeds then are roasted for 10-20 minutes, depending on their size, to achieve a yellowish color.

H) The roasted seeds are then ground through a heavy duty seed crusher into a fine powder.

I) This powder is added to 300 ml of distilled water, left for two hours of infusion, then stirred and filtered very finely to remove all the residuals into a 350 ml solution rich in the nutrients, minerals, vitamins and oils of the seeds called S2.

J) In addition, 15-20 grams of green tea leaves are added to 330 ml of distilled water, left for two hours of infusion, then stirred and filtered very finely to remove all the residuals into a 350 ml solution, called S3, rich in the nutrients of green tea, used 100% of it for oily hair/scalp, or 50% of it for dry or normal hair/scalp and the balance of 50% will be distilled water.

K) 51 is put into a new mixing container, then 350-700 grams of honey, depending on type, balance compensated for with distilled water is added. Then S2 and S3 are added, stirred and mixed together to create an encompassing mixture referred to as S4.

L) S4 is passed through a filtration system, to remove particles and residuals while maintaining the chemical composition of the product, and poured into bottles.

M) 700 ml of olive oil is added to the bottle containing the S4 solution, creating the solution S5.

N) The bottle is shaken very well, and left for 1-2 days to settle and mix, creating the final solution, the subject of this invention S6 of around 7.142 Liters.

Mixing and Preparation of Hair Spray

For the creation of 1 Liter of the final formulation solution:

A) Make 20 ml of S1.

B) Make 980 ml of S2.

The hairspray shall be used after use of the above mentioned hair lotion/solution and contains 2-5 vol.-% of the above bioethanol extracted from dates and date seeds with distilled water.

Dosage and Treatment of Inventive Hair Spray

Treating hair loss and dandruff generally includes applying 10-20 ml, every other day, dependent on condition severity and hair density, directly on the scalp and hair using the dropper of the bottle's nozzle, the user should not pour it into their hands, and should massage their hair gently without rubbing, and make sure to cover their hair and scalp completely until the tips of the hairs, then, applying the spray, and then comb it gently and let it sit a minimum of five hours (twenty four hours maximum). It is preferable for the user to sleep with it through the night.

After application as described, a user can wash with an herbal shampoo and after washing and towel drying then use the spray again and user can comb or blow dry his or her hair, it is now finished.

The Effects of the Finished Product Containing all the Previous Ingredients

The scope of this invention also deals with the final product effects on hair, scalp, and dandruff countering.

Based on trials conducted on behalf of the inventor for a period of two months at the Skin Institute, Neuchatel/Switzerland, results show significant initial capability of the inventive formulation as to the:

A) reduction of hair loss up to 33%, even though one of the trial people had severe skin problem (psoriasis); and B) reduction of dandruff up to 90%.

Figure 2:
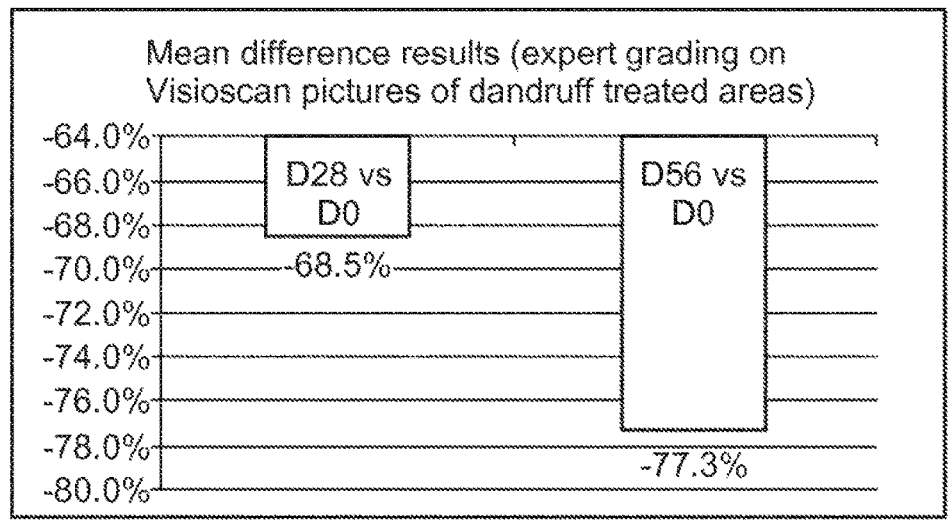
FIG. 2 is a graph showing the reduction in dandruff realized with treatments of the composition of the Example.
Figure 3:
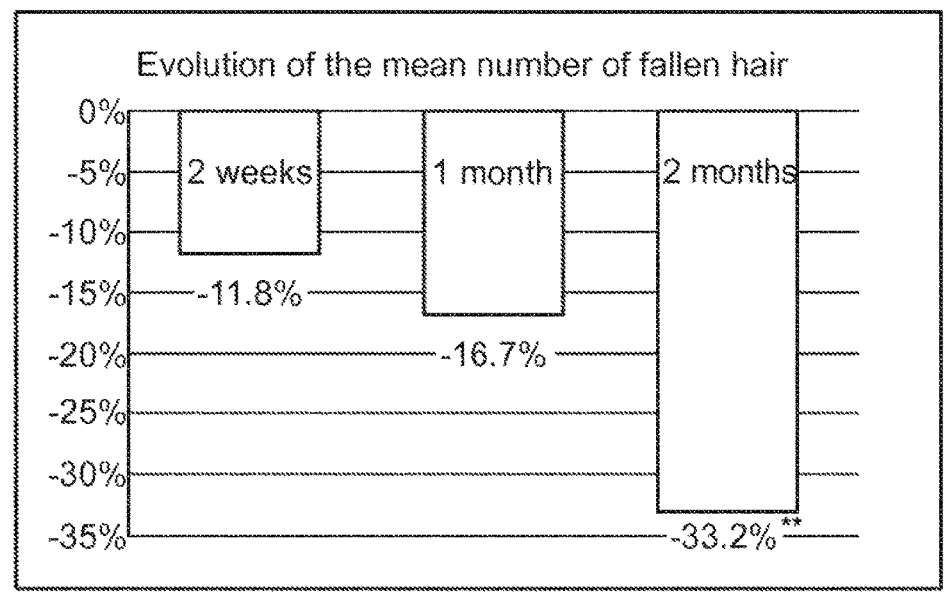
FIG. 3 is a graph showing the reductions in the mean number of fallen hair realized with treatments of the composition of the Example for periods of 2 weeks, 1 month, and 2 months.

The graphs presented in FIG. 2 (reduction of dandruff) and FIG. 3 (reduction of fallen hair) show significant results on the trial's volunteers in Switzerland.

The Skin Institute also observed, using VISIOSCAN, that there is a lot of hair growth on the treated area. Currently, the formulation product is undergoing Trichoscan trials as presented in Table 1.

TABLE 1

|  | D 28 vs D 0 | D 56 vs D 0 |
| --- | --- | --- |
| 1001 | −78.6% | −100.0% |
| 1002 | −70.6% | −58.8% |
| 1003 | — | −63.3% |
| 1004 | −51.3% | −93.3% |
| 1005 | −55.2% | −82.8% |
| 1006 | −86.8% | −65.8% |
| Mean results | −68.5% | −77.3% |

Having illustrated and described the principles of the present invention, it should be apparent to persons skilled in the art that the invention can be modified in arrangement and detail without departing from such principles.

Although the materials and methods of this invention have been described in terms of various embodiments and illustrative examples, it will be apparent to those of skill in the art that variations can be applied to the materials and methods described herein without departing from the concept, spirit and scope of the invention. All such similar substitutes and modifications apparent to those skilled in the art are deemed to be within the spirit, scope and concept of the invention as defined by the appended claims.

What is claimed is:

1. A formulation for the treatment of hair, the formulation comprising a date-based ethanol-containing distillate and a date seed infusion, wherein:

a) the date-based ethanol-containing distillate is produced by a process comprising:

i) forming a fermentation mixture that comprises dates with their seeds, date molasses, water, and yeast *Saccharomyces cerevisiae;* ii) fermenting the fermentation mixture;

iii) performing a first distillation of the fermented mixture to remove methanol from the fermented mixture; and iv) performing a second distillation of the fermented mixture to form the date-based ethanol-containing distillate that comprises at least 82% by volume ethanol; and b) the date seed infusion is produced by a process comprising:

i) roasting date seeds;

ii) grinding the roasted date seeds to form a date seed powder;

iii) mixing the date seed powder and water to extract nutrients, minerals, vitamins, and oils from the date seed powder; and iv) separating the extracted date seed nutrients, minerals, vitamins, and oils from the date seed powder to form the date seed infusion.

2. The formulation of claim 1 consisting of the date-based ethanol-containing distillate and a date seed infusion.

3. The formulation of claim 1, wherein the date-based ethanol-containing distillate and the date seed infusion are constituents of an encompassing mixture that further comprises one or more of the following: a green tea infusion, honey, and water; and the formulation further comprises olive oil.

4. The formulation of claim 3, wherein the encompassing mixture comprises the date-based ethanol-containing distillate, the date seed infusion, the green tea infusion, the honey, and the water.

5. The formulation of claim 4, wherein:

the encompassing mixture consists of the date-based ethanol-containing distillate, the date seed infusion, the green tea infusion, honey, and water; and the formulation consists of the encompassing mixture and the olive oil.

6. The formulation of claim 4, wherein:

the encompassing mixture and olive oil are at a volume ratio of about 9:1;

the date-based ethanol-containing distillate, the date seed infusion, green tea infusion, honey, and water of the encompassing mixture are at a volume ratio of about 1:0.07:0.07:0.05-0.1:0.1-0.05;

the date-based ethanol-containing distillate comprises at least 82% by volume ethanol; and the date-based ethanol-containing distillate is no more than 60% by volume of the formulation.

\* \* \* \* \*